United States Patent
Yamane et al.

(12)

(10) Patent No.: US 6,891,048 B2
(45) Date of Patent: May 10, 2005

(54) GLYCOLIDE PRODUCTION PROCESS, AND GLYCOLIC ACID COMPOSITION

(75) Inventors: Kazuyuki Yamane, Fukushima (JP); Yukichika Kawakami, Fukushima (JP)

(73) Assignee: Kureha Kagaku Kogyo KK, Tokyo (JP)

( * ) Notice: Subject to any disclaimer, the term of this patent is extended or adjusted under 35 U.S.C. 154(b) by 0 days.

(21) Appl. No.: 10/469,741

(22) PCT Filed: Mar. 5, 2002

(86) PCT No.: PCT/JP02/02025

§ 371 (c)(1),
(2), (4) Date: Sep. 4, 2003

(87) PCT Pub. No.: WO02/070508

PCT Pub. Date: Sep. 12, 2002

(65) Prior Publication Data

US 2004/0087805 A1 May 6, 2004

(30) Foreign Application Priority Data

Mar. 6, 2001 (JP) ........................................ 2001-062436

(51) Int. Cl.[7] ........................ C07D 319/12; C07C 59/06
(52) U.S. Cl. ........................................ 549/274; 562/579
(58) Field of Search ........................... 549/274; 562/579

(56) References Cited

U.S. PATENT DOCUMENTS

| 2,668,162 A | 2/1954 | Lowe |
| 4,727,163 A | 2/1988 | Bellis |
| 4,835,293 A | 5/1989 | Bhatia |
| 5,023,349 A | 6/1991 | Bhatia |
| 5,830,991 A | 11/1998 | Shiiki et al. |

FOREIGN PATENT DOCUMENTS

FR    2692263    12/1993

*Primary Examiner*—Bernard Dentz
(74) *Attorney, Agent, or Firm*—Dinsmore & Shohl LLP

(57) ABSTRACT

The invention provides a process for producing glycolide by depolymerization by heating of a glycolic acid oligomer in the presence or absence of a solvent, which process ensures stable depolymerization. The depolymerization reaction is carried out while the content of alkaline metal ions in a glycolic acid oligomer-containing depolymerization reaction system is controlled to 0.001% by mass or lower; a sulfate or an organic acid salt, each in the form of di- or poly-valent cations, or a mixture thereof is allowed to be present as a stabilizer in the depolymerization reaction system; or the content of alkaline metal ions in the depolymerization reaction system is controlled to 0.001% by mass or lower, and a sulfate or an organic acid salt, each in the form of di- or poly-valent cations, or a mixture thereof is allowed to be present as a stabilizer in the depolymerization reaction system.

25 Claims, No Drawings

GLYCOLIDE PRODUCTION PROCESS, AND GLYCOLIC ACID COMPOSITION

This application is a 371 of PCT/JP02/02025 filed Mar. 5, 2002.

FIELD OF THE INVENTION

The present invention relates generally to a process for the production of glycolide that is a cyclic dimer ester of glycolic acid, and more particularly to a process for producing glycolide by depolymerization by heating of a glycolic acid oligomer, which ensures that the depolymerization reaction can be carried out in a stable manner, thereby obtaining glycolide economically yet efficiently.

The glycolide obtained by the production process of the invention is well suited as the starting material for polyglycolic acid and glycolic acid copolymers that are useful biodegradable polymers and polymers having gas barrier properties, etc.

BACKGROUND OF THE INVENTION

Polyglycolic acid is a polyester formed by dehydration-polycondensation of glycolic acid (i.e., α-hydroxyacetic acid) and having the following formula:

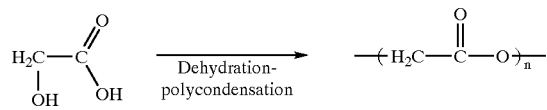

Here n stands for the number of repeating units.

Polyglycolic acid is a biodegradable polymer that is hydrolyzed in vivo and, in natural environments, is metabolized and decomposed by microorganisms into water and carbonic acid gas. For this reason, the polyglycolic acid now attracts attention as environment-friendly polymer substitutes for medical materials or general-purpose resins as well as materials having gas barrier properties. However, it is still difficult to obtain any polyglycolic acid having a high molecular weight by means of the dehydration-polycondensation of glycolic acid.

According to another polyglycolic acid production process so far known in the art, glycolide that is a cyclic dimer ester of glycolic acid is first synthesized. Then, this glycolide is subjected to ring-opening polymerization in the presence of a catalyst (e.g., stannous octoate). The resultant polymer is a polyglycolic acid that is often called polyglycolide because it is a ring-opened polymer of glycolide.

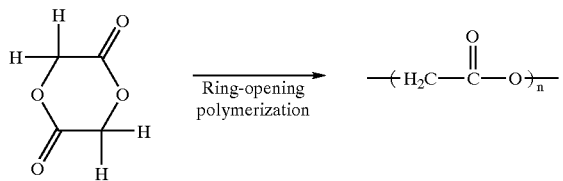

Here n is the number of repeating units.

To produce polyglycolic acid having a high molecular weight by the ring-opening polymerization of glycolide, it is required to use high-purity glycolide as the starting material. To use glycolide as the starting material to produce polyglycolic acid on an industrial scale, it is thus essential to establish the technical means capable of economically feeding such high-purity glycolide.

Glycolide is a cyclic ester compound having the structure wherein two water molecules are eliminated from two glyclolic acid molecules. Only by the esterification reaction of glycolic acid by means of direct dehydration, however, any glycolide cannot be. So far, various glycolide production processes have been proposed.

U.S. Pat. No. 2,668,162 discloses a process in which a glycolic acid oligomer is crushed into powders and heated at 270 to 285° C. under an ultra-high vacuum (12 to 15 Torr (1.6 to 2.0 kPa)) while the powders are fed to a reaction vessel in small portions (about 20 g/hr) for depolymerization, and the resultant glycolide-containing vapor is entrapped. This process, albeit being suitable for small-scale production, is found to have difficulty in large-scale production and so unsuitable for mass production. In addition, this process causes the oligomer to become heavy upon heating and so remain in the form of much residues in the reaction vessel, resulting in decreased glycolide yields and the need of cleaning off the residues. To add to this, the process makes glycolide (having a melting point of 82 to 83° C.) and byproducts likely to separate out in recovery lines, ending up with troubles such as line clogging.

U.S. Pat. No. 4,727,163 shows a glycolide production process wherein a polyether having good thermal stability is used as a substrate, a small amount of glycolic acid is then block copolymerized with the substrate to obtain a block copolymer, and the copolymer is finally heated for depolymerization. However, this block copolymerization process is intractable and incurs some considerable production cost. In addition, the process makes glycolide and byproducts likely to separate out in recovery lines, leading to troubles such as line clogging.

U.S. Pat. Nos. 4,835,293 and 5,023,349 teach a process wherein an α-hydroxycarboxylic acid oligomer such as a polyglycolic acid oligomer is heated into a melt, and a cyclic dimer esters such as glycolide generated and vaporized out of the surface of the melt is entrained in an inert gas such as nitrogen gas and stripped in a low-boiling solvent such as acetone or ethyl acetate for recovery. With this process, it is still difficult to cut back on production costs, because of problems such as a slow formation rate of the cyclic dimer ester, possible formation of heavy materials in the melt, and the need for preheating for blowing a large amount of inert gas into the melt.

French Patent No. 2692263-A1 discloses a process for the production of a cyclic dimer ester wherein an oligomer of an α-hydroxycarboxylic acid or its ester or salt is added to a solvent with a catalyst added thereto, and then stirred in the presence of heat for catalytic decomposition. This process is carried out under normal or applied pressure, using a solvent suitable for entraining the cyclic dimer ester therein in a gaseous phase state. The gaseous phase is then condensed for the recovery of the cyclic dimer ester and solvent. The specification refers to only an example wherein a lactic acid oligomer is used as the raw feed and dodecane (having a boiling point of about 214° C.) is employed as the solvent. However, the results of follow-up experimentation made by the inventors under the same conditions as described in the example and using a glycolic acid oligomer and dodecane showed that heavy materials begin to form simultaneously with the start of the depolymerization reaction, the formation of glycolide stops at a point of time when a very slight amount of glycolide is formed, and much labor is needed for cleaning reaction residues because they are too viscous.

JP-A 09-328481 filed by the applicant of this application (U.S. Pat. No. 5,830,991) discloses a process comprising the steps of heating and depolymerizing an α-hydroxycar-boxylic acid oligomer such as a glycolic acid oligomer in a polar organic solvent having a high boiling point, and distilling off the resultant cyclic dimer ester such as glycolide together with the polar organic solvent, and removing the cyclic dimer ester from the distillates.

The results of the inventors' subsequent investigation have showed that if a polyalkylene glycol ether having satisfactory thermal stability is used as the polar organic solvent in this process, cost reductions can then be achieved by recycling the solvent. When a glycolic acid oligomer synthesized with a commercially available industrial-grade aqueous solution of glycolic acid is depolymerized in a high-boiling polar organic solvent, however, it is difficult to obtain high-purity glycolide economically yet in high yields, because the reaction solution turns black within a relatively short time and heavy materials are deposited onto the wall surface of the reaction vessel.

In view of such technical levels, further improvements are required for the purpose of producing high-purity glycolide on an industrial scale yet efficiently as well as low cost.

OBJECTS AND SUMMARY OF THE INVENTION

One object of the present invention is to provide a process for the production of glycolide by depolymerization of a glycolic acid oligomer, which enables a depolymerization reaction to be carried out in a stable manner so that glycolide can be produced economically yet efficiently.

Another object of the invention is to provide a glycolic acid composition that is a raw material for the glycolic acid oligomer, which enables the depolymerization reaction to be carried out in a stable manner.

As a result of inventors' tracking-down of the cause of why, when a glycolic acid oligomer synthesized using an industrial-grade aqueous solution of glycolic acid—that is supplied for the purpose of industrial-scale production—is depolymerized, the depolymerization reaction system becomes unstable within a relatively short time, it has been found that a trace amount of alkaline metal ions contained in the glycolic acid oligomer is ascribable to that cause.

As a consequence of the depolymerization reaction of a glycolic acid oligomer synthesized by purifying or otherwise processing an industrial-grade aqueous solution of glycolic acid to lower its alkaline metal ion content to a specific limit or less, it has been found that the depolymerization reaction can be kept stable over an extended period of time.

Even with an industrial-grade aqueous solution of glycolic acid, it has again been found that if a glycolic acid oligomer is synthesized by adding thereto a sulfate and/or an organic acid salt, each in the form of di- or poly-valent cations, it is then possible to ensure the long-term stability of the depolymerization reaction even in the presence of alkaline metal ions, because the sulfate and/or organic acid salt contained in the oligomer in the form of di- or poly-valent cations act as a stabilizer. By using a glycolic acid oligomer wherein the alkaline metal ion content is reduced as much as possible and at least one salt selected from the group consisting of the sulfates and organic acid salts, each in the form of di- or poly-valent cations, is contained as a stabilizer, it has further been found that the long-term stability of depolymerization can be much more improved.

The depolymerization reaction system used herein, for instance, includes a system composed substantially of a glycolic acid oligomer alone, and a system comprising a glycolic acid oligomer and a solvent optionally with other components such as a solubilizer. In the invention, it is advantageous to control the content of alkaline metal ions in these depolymerization reaction systems and allow the sulfate and/or organic acid salt, each in the form of di- or poly-valent cations, to be present therein. When the solvent, solubilizer and so on are used in addition to the glycolic acid oligomer, it is also favorable to control the content of alkaline metal ions in these subcomponents.

The high-boiling, non-basic organic compound suitable as the solubilizer, even when it is not used in combination with any other organic solvent, enables the depolymerization reaction of the glycolic acid oligomer to proceed smoothly.

These findings have underlain the present invention.

Thus, the present invention provides a process for the production of glycolide by depolymerization by heating of a glycolic acid oligomer in the presence or absence of a solvent, characterized in that a depolymerization reaction is carried out while:

(1) the content of alkaline metal ions in a glycolic acid oligomer-containing depolymerization reaction system is controlled to 0.001% by mass or lower, (2) a sulfate or an organic acid salt, each in the form of di- or poly-valent cations, or a mixture thereof is allowed to exist as a stabilizer in the depolymerization reaction system, or (3) the content of alkaline metal ions in the depolymerization reaction system is controlled to 0.001% by mass or lower, and a sulfate or an organic acid salt, each in the form of di- or poly-valent cations, or a mixture thereof is allowed to exist as a stabilizer in the depolymerization reaction system.

According to the invention, there is also provided a glycolic acid composition in which 0.01 to 10 grams of a sulfate or an organic acid salt, each in the form of di- or poly-valent cations, or a mixture thereof is contained per mole of glycolic acid.

BEST MODE FOR CARRYING OUT THE INVENTION

1. Depolymerization Reaction System

By way of example but not by way of limitation, the depolymerization method usable herein includes melt depolymerization (U.S. Pat. No. 2,668,162), solution depolymerization (U.S. Pat. No. 5,830,991 corresponding to JP-A 09-328481), and solid-phase depolymerization.

Thus, the "glycolic acid oligomer-containing depolymerization reaction system" used herein is understood to refer to a system composed substantially of a glycolic acid oligomer alone and free of any solvent, and a system comprising a glycolic acid oligomer and a solvent, depending on the depolymerization method used.

2. Alkaline Metal Ions

The alkaline metal ions that must be reduced in terms of their amount to be present in the depolymerization reaction system include those of alkaline metals such as lithium, sodium, potassium, rubidium and cesium. Sodium ions and potassium ions are likely to be contained in larger amounts than the rest. More specifically, a commercially available industrial-grade aqueous solution of glycolic acid contains a trace amount of sodium ions; in most cases, a 70% by mass aqueous solution of glycolic acid contains sodium ions in an amount exceeding 0.01% by mass. A glycolic acid oligomer obtained by the dehydration-depolymerization of an aqueous solution of glycolic acid containing 0.01% by mass of sodium ions contains sodium ions in an amount of the order of 0.02% by mass.

3. How the Content of Alkaline Metal Ions is Reduced

In the invention, the depolymerization reaction system should preferably be substantially free of any alkaline metal ions. Because the quantification limit to the method herein used for the measurement of alkaline metal ions is 0.001% by mass, it is preferable to control the content of alkaline metal ions in the depolymerization reaction system to 0.001% by mass or lower, and especially to less than 0.001% by mass. As the content of alkaline metal ions in the depolymerization reaction system is too high, some inconveniences are likely to occur; for instance, the depolymerization reaction system turns black within a relatively short time during the depolymerization reaction by heating at high temperature, the glycolide product is contaminated with impurities, and heavy materials are deposited onto the wall surface of a reaction vessel. If the sulfate and/or organic acid salt, each in the form of di- or poly-valent cations, are allowed to exist as the stabilizer in the depolymerization reaction system, the stability of the depolymerization reaction may then be maintained even when the content of alkaline metal ions is high. However, in this case, too, it is desirable to reduce the content of alkaline ions in the depolymerization reaction system, thereby making the stability much higher.

Alkaline metal ions may be substantially eliminated from within the depolymerization reaction system by decreasing the content of alkaline metal ions in the glycolic acid oligomer, decreasing the content of alkaline metal ions in other components such as the solvent and solubilizer or the like. In the invention, the content of alkaline metal ions should preferably be reduced by using these means in combination.

The alkaline metal ions are often brought in the depolymerization reaction system via the glycolic acid oligomer used for the depolymerization reaction. It is thus desired to decrease the content of alkaline metal ions in the glycolic acid oligomer. To decrease the content of alkaline metal ions in the glycolic acid oligomer, it is advantageous to purify glycolic acid or its aqueous solution that is the starting material, thereby decreasing the content of alkaline metal ions therein. Alternatively, reliance may be placed on a glycolic acid alkyl ester free from any alkaline metal ions.

The glycolic acid oligomer may be obtained by the condensation reaction of glycolic acid, glycolic acid ester or glycolic acid salt. By use of glycolic acid, glycolic acid ester or glycolic acid salt substantially free from any alkaline metal ions, it is possible to obtain a glycolic acid oligomer with a considerably decreased alkaline metal ion content. For instance, a glycolic acid containing no alkaline metal ions may be obtained by deionizing an industrial-grade aqueous solution of glycolic acid through an ion exchange resin, recrystallizing glycolic acid, or the like.

A high-purity glycolic acid may be obtained by distilling or otherwise purifying a glycolic acid alkyl ester, preferably a glycolic acid alkyl ester having a $C_1$ to $C_4$ alkyl ester group, and then hydrolyzing the resulting product. The purification by distillation, because of being simpler than the recrystallization of glycolic acid, is well fit for commercialization. The glycolic acid oligomer substantially free from any alkaline metal ion may also be obtained by the condensation of the purified glycolic acid alkyl ester. The condensation reaction of the glycolic acid alkyl ester makes it possible to dispense with any step for hydrolysis to glycolic acid.

A glycolic acid oligomer obtained by the condensation of a mixture of glycolic acid substantially free from any alkaline metal ion and a glycolic acid alkyl ester, too, may be suitable for the glycolic acid oligomer used herein. This mixture may be obtained by adding glycolic acid to the glycolic acid alkyl ester or, alternatively, hydrolyzing a part of the glycolic acid alkyl ester. By use of this mixture, it is possible to make the reaction rate faster than could be achieved with the sole condensation reaction of the glycolic acid alkyl ester.

The glycolic acid alkyl ester is synthesized by the reduction reaction of a dialkyl oxalate, the alcoholysis of a glycolic acid oligomer or the like, and purified by distillation, etc. Glycolic acid alkyl esters having $C_1$ to $C_4$ alkyl ester groups are preferred in view of ease of distillation, ease of hydrolysis and ease of direct condensation reaction, although methyl glycolate is most preferred.

When other components such as the solvent and solubilizer are incorporated in the depolymerization reaction system, the content of alkaline metal ions contained therein should preferably be reduced to 0.001% by mass or lower, and especially to less than 0.001% by mass. These components may be purified by distillation, deionization with an ion exchange resin, etc.

4. Sulfate and/or Organic Acid Salt. Each in the Form of Di- or Poly-Valent Cations Upon the depolymerization by heating of glycolic acid oligomers, some unfavorable phenomena are likely to occur; for instance, a depolymerization reaction solution is considerably colored, heavy materials are formed and deposited onto the wall surface of a reaction vessel, and distillates are contaminated. This goes true particularly for the case where alkaline metal ions are substantially present in depolymerization reaction systems. If the sulfate and/or organic acid salt, each in the form of di- or poly-valent cations, are allowed to exist as the stabilizer in a depolymerization reaction system according to the process of the invention to stabilize a depolymerization reaction, it is then possible to eliminate such phenomena.

The sulfate in the form of di- or poly-valent cations, for instance, includes metal sulfates such as magnesium sulfate, nickel sulfate, iron sulfates, copper sulfates, zinc sulfate, zirconium sulfate and aluminum sulfate. Usually but not exclusively, the cations may be divalent, trivalent, or tetravalent. Ferric sulfate and cupric sulfate are typical of iron sulfates and copper sulfates, respectively. Of these sulfates, ferric sulfate is advantageous in view of cost. For the organic acid salt, use may be made of di- or poly-valent cationic salts of aliphatic acids, aromatic acids, etc. The organic acid that is a conjugate acid, for instance, includes aliphatic carboxylic acids such as formic acid, acetic acid, oxalic acid, malonic acid, succinic acid, glutaric acid, lactic acid, glycolic acid, butanoic acid, pentanoic acid, hexanoic acid, heptanoic acid, octanoic acid, dodecanoic acid, stearic acid and oleic acid; aromatic carboxylic acids such as phthallic acid, benzoic acid and salicylic acid; and so on. Of these, the aliphatic carboxylic acids are preferred, although particular preference is given to α-hydroxyacetic acid such as lactic acid and glycolic acid. For di- or poly-valent cations of the organic acid salts, for instance, reference is made to magnesium, nickel, iron, copper, zinc, zirconium, and aluminum. Usually but not exclusively, the cations are divalent, trivalent, or tetravalent. Of these organic acid salts, aluminum lactate is preferably used. These organic acid salts may be used alone or in combination of two or more or, alternatively, they may be used in combination with the sulfate. These sulfates and organic acid salts may be used alone or in combination of two or more.

The sulfate and/or organic acid salt in the form of di- or poly-valent cations should preferably be allowed to exist in the depolymerization reaction system by adding them to the glycolic acid oligomer-containing depolymerization reaction system, incorporating them into the glycolic acid oligomer, and so on. To incorporate the sulfate and/or organic acid salt in the form of di- or poly-valent cations into a glycolic acid oligomer, the glycolic acid oligomer may be synthesized while the sulfate and/or organic acid salt in the form of di- or poly-valent cations are added to the raw material such as glycolic acid.

Usually, the amount of the di- or poly-valent cations present in the depolymerization reaction system should be in the range of 0.001 to 5% by mass, preferably 0.01 to 3% by mass, and more preferably 0.05 to 2% by mass. In most cases, the long-term stabilization of the depolymerization reaction can be achieved by allowing 0.05 to 0.5% by mass of di- or poly-valent cations to exist in the depolymerization reaction system.

When the amount of alkaline metal ions contained in the glycolic acid oligomer is known, it is preferable that at the time of glycolic acid oligomer synthesis, the content of di- or poly-valent cations is controlled in such a way as to be in the range of 1 to 100 times (on a mass basis), especially 1.5 to 30 times, and more especially 2 to 5 times as large as the amount of alkaline metal ions. As the content of di- or poly-valent cations is too low, no sufficient effect on stabilization is achievable. Too much causes the effect on stabilization to be saturated, resulting in cost increases and an increase in the volume of the depolymerization reaction system. When the amount of alkaline metal ions contained in the glycolic acid oligomer is known, it is acceptable to add the sulfate and/or organic acid salt in the form of di- or poly-valent sulfate cations to the depolymerization reaction system at the aforesaid quantitative ratio.

If the sulfate and/or organic acid salt in the form of di- or poly-valent cations are allowed to exist as the stabilizer in the depolymerization reaction system and, at the same time, the content of alkaline metal ions is controlled to 0.001% by mass or lower, the depolymerization reaction can then be much more stabilized.

5. Synthesis of Glycolic Acid Oligomer

Glycolic acid oligomers may be synthesized by heating glycolic acid, glycolic acid ester or glycolic acid salt to usually 100 to 250° C., and preferably 140 to 230° C. under reduced pressure, normal pressure or applied pressure and, if required, in the presence of a condensation catalyst or an ester exchange catalyst, so that a condensation reaction or an ester exchange reaction is carried out until distillation of low-molecular-weight materials such as water and alcohol is not substantially found.

If a purified glycolic acid product with a decreased alkaline metal ion content is used as the starting material such as glycolic acid, the content of alkaline metal ions in the glycolic acid oligomer can then be reduced ahead. If the sulfate and/or organic acid salt in the form of di- or poly-valent cations are added to the reaction system, the di- or poly-valent cations can then be contained ahead in the glycolic acid oligomer.

The resulting glycolic acid oligomer may be used directly for the depolymerization reaction. If the resulting glycolic acid oligomer is washed with a non-solvent such as benzene or toluene, unreacted or low-molecular-weight materials can then be removed therefrom. In consideration of glycolide yields, the glycolic acid oligomer used should have a melting point of usually 140° C. or higher, preferably 160° C. or higher, and more preferably 180° C. or higher. The "melting point (Tm)" used herein is understood to mean a melting point detected with a differential scanning calorimeter (DSC) while a sample is heated at a rate of 10° C./min. in an inert gas atmosphere.

6. Depolymerization Reaction

As already explained, the depolymerization reaction of glycolic acid oligomers, for instance, may be carried out by means of melt depolymerization, solution depolymerization, solid-phase depolymerization, etc. Of these, the solution depolymerization, and the solid-phase depolymerization is carried out using substantially a glycolic acid oligomer alone in the absence of any solvent. To mass produce glycolide in a stable manner yet on an industrial scale, however, it is preferable to make use of the solution depolymerization wherein glycolic acid oligomers are de polymerized in the presence of a solvent such as an organic or inorganic solvent.

7. Solution Depolymerization

A solution depolymerization process preferably used herein includes such steps (I), (II) and, (III) as mentioned below.

(I) A mixture comprising a glycolic acid oligomer and an organic solvent having a boiling point of 230 to 450° C. is heated under normal pressure or reduced pressure to dissolve the glycolic acid oligomer in the organic solvent until the proportion of a glycolic acid oligomer melt phase in the mixture is reduced down to 0.5 or less.

(II) The solution obtained at step (I) is heated under normal pressure or reduced pressure to depolymerize the glycolic acid oligomer, and the glycolide formed by depolymerization is co-distilled together with the organic solvent out of the depolymerization reaction system.

(III) Glycolide is recovered from the distillates obtained by distillation.

If, at step (II), fresh feeds of the glycolic acid oligomer and organic solvent are added into the depolymerization reaction system during or after the glycolide and organic solvent are co-distilled out, it is then possible to carry out depolymerization continuously or repeatedly.

The high-boiling organic solvent should be used in amounts of usually 0.3 to 50 times (on a mass basis), preferably 0.5 to 20 times, and more preferably 1 to 10 times as large as that of the glycolic acid oligomer. A mixture comprising a glycolic acid oligomer and an organic solvent, if required, with additives such as a solubilizer is heated to a temperature of usually 230° C. or higher under normal pressure or reduced pressure to dissolve the whole, or a substantial, portion of the oligomer in the organic solvent. More exactly, the glycolic acid oligomer is dissolved in the organic solvent until the proportion of a glycolic acid oligomer melt phase in the mixture is reduced down to 0.5 or lower.

Where a substantial portion of glycolic acid oligomer is not dissolved in the organic solvent, the proportion of the oligomer melt phase becomes too high to distill out glycolide. In addition, heavy material-formation reactions are likely to occur in the oligomer melt phase. By depolymerizing the glycolic acid oligomer in a solution state, the formation rate of glycolide generated and vaporized out of the surface of the oligomer can be much more increased. In this regard, it is preferable that upon the mixture heated to a temperature at which depolymerization occurs, the glycolic acid oligomer is already completely dissolved in the organic solvent; the melt phase is kept against any phase separation.

It is here noted that the term "proportion of the glycolic acid oligomer melt phase" refers to the volume ratio of the oligomer melt phase formed in an actually used organic solvent with the proviso that the volume of the oligomer melt phase formed in a solvent such as liquid paraffin, in which the glycolic acid oligomer is substantially insoluble, is 1.

Heating is carried out under normal pressure or reduced pressure; however, it should preferably be done under a reduced pressure of about 0.1 to 90 kPa. Heating should desirously be performed in an inert atmosphere. The mixture is heated to at least 230° C., at which the depolymerization reaction of glycolic acid oligomer occurs. However, usually, the mixture is heated to temperatures of 230 to 320° C., preferably 235 to 300° C., and more preferably 240 to 290° C.

By heating, the depolymerization of glycolic acid oligomer takes place and glycolide is co-distilled out together with the organic solvent. Since the resultant glycolide is co-distilled out together with the organic solvent, it is possible to prevent any deposition of glycolide on the wall surfaces of a reaction vessel and lines, which may otherwise cause accumulation of glycolide. The distillates are then guided out of the depolymerization reaction system to recover glycolide therefrom. The distillates are cooled, if required, with a nonsolvent added thereto, so that glycolide is separated out and solidified. The separated-out glycolide is isolated from the mother liquor by means of filtration, centrifugal sedimentation, decantation, etc. If required, the isolated glycolide is washed or extracted with a non-solvent such as cyclohexane or ether, and then recrystallized with ethyl acerate or the like. The glycolide may also be purified by distillation.

The mother liquor, from which glycolide has been isolated, may be recycled without any purification. Alternatively, the mother liquor may be filtered out and purified by treatment with activated carbon, etc. for recycling purposes. Still alternatively, the mother liquor may be redistilled and purified for recycling purposes.

As glycolide is co-distilled out of the depolymerization reaction system together with the organic solvent, there is a decrease in the volume of the depolymerization reaction system. If the fresh amounts of the glycolic acid oligomer and organic solvent—that make up for the amount of distillates—are additionally fed to the reaction system, it is then possible to carry out a continuous or repetitive depolymerization reaction process. According to the production process of the invention, the depolymerization reaction can be carried out in a stable manner, and so such a process can be used, thereby making striking improvements in production efficiency and cutting back on cost.

8. Organic Solvent

High-boiling organic solvents having a boiling point of 230 to 450° C. are preferable for the organic solvent used in the aforesaid solution depolymerization. The organic solvent used herein should preferably have a molecular weight in the range of 150 to 450. When an organic solvent having too low a boiling point is used, no high depolymerization reaction temperature can be set so that the rate of formation of glycolide becomes low. When an organic solvent having too high a boiling point, on the other hand, the organic solvent is hardly distilled out upon the depolymerization reaction, and so any co-distillation of the organic solvent and the glycolide formed by depolymerization becomes difficult. The boiling point of the organic solvent used should be in the range of preferably 235 to 450° C., more preferably 260 to 430° C., and most preferably 280 to 420° C. When the molecular weight of the organic solvent used deviates from the aforesaid range, any co-distillation of the organic solvent and glycolide becomes difficult. The molecular weight of the organic solvent used should be in the range of preferably 180 to 450, and more preferably 200 to 400.

The high-boiling organic solvent, for instance, includes alkoxyalkyl esters of aromatic carboxylic acids, alkoxyalkyl esters of aliphatic carboxylic acids, polyalkylene glycol ethers, polyalkylene glycol esters, aromatic carboxylic esters, aliphatic carboxylic esters, and aromatic phosphoric esters. For the organic solvent, it is preferable to use polar organic solvents having in their molecule atoms such as N, O and P and a polar group such as a hydroxyl group and a carboxyl group and having an electronically biased structure.

Preferable examples of the aromatic carboxylic ester are aromatic dicarboxylic diesters such as phthallic esters, e.g., dibutyl phthalate, dioctyl phthalate, dibenzyl phthalate and benzylbutyl phthalate; and benzoic esters, e.g., benzyl benzoate, and preferable examples of the aliphatic carboxylic ester are aliphatic dicarboxylic diesters such as adipic esters, e.g., octyl adipate and sebacic esters, e.g., dibutyl sebacate.

Preferably in the invention, a polyalkylene glycol diether having the following formula (1) should be used as the organic solvent:

$$X^1 - O - (R^1 - O)_p - Y \qquad (1)$$

Here $R^1$ is a methylene group or a branched-chain or straight-chain alkylene group having 2 to 8 carbon atoms, $X^1$ and Y are each a hydrocarbon group, and p is an integer of 1 or greater provided that when p is an integer of 2 or greater, a plurality of $R^1$s may be identical with or different from each other.

Exemplary such polyalkylene glycol diethers are polyethylene glycol dialkyl ethers such as diethylene glycol dibutyl ether, diethylene glycol dihexyl ether, diethylene glycol dioctyl ether, triethylene glycol dimethyl ether, triethylene glycol diethylene ether, triethylene glycol dipropyl ether, triethylene glycol dibutyl ether, triethylene glycol dihexyl ether, triethylene glycol dioctyl ether, tetraethylene glycol dimethyl ether, tetraethylene glycol diethyl ether, tetraethylene glycol dipropyl ether, tetraethylene glycol dibutyl ether, tetraethylene glycol dihyexyl ether, tetraethylene glycol dioctyl ether, diethylene glycol butylhexyl ether, diethylene glycol butyloctyl ether, diethylene glycol hexyloctyl ether, triethylene glycol butylhexyl ether, triethylene glycol butyloctyl ether, triethylene glycol hexyloctyl ether, tetraethylene glycol butylhexyl ether, tetraethylene glycol butyloctyl ether and tetraethylene glycol hexyloctyl ether as well as polyalkylene glycol dialkyl ethers wherein the ethyleneoxy groups in these polyethylene glycol dialkyl ethers are substituted by propyleneoxy or butyleneoxy groups, e.g., polypropylene glycol dialkyl ethers or polybutylene glycol dialkyl ethers; diethylene glycol butylphenyl ether, diethylene glycol hexylphenyl ether, diethylene glycol octylphenyl ether, triethylene glycol butylphenyl ether, triethylene glycol hexylphenyl ether, triethylene glycol octylphenyl ether, tetraethylene glycol butylphenyl ether, tetraethylene glycol hexylphenyl ether and tetraethylene glycol octylphenyl ether, polyethylene glycol alkylaryl ethers wherein the hydrogen groups in the phenyl groups in these compounds are substituted by an alkyl group, an alkoxy group or a halogen atom, and polyalkylene glycol alkylaryl ethers such as polypropylene glycol alkylaryl ethers or polybutylene glycol alkylaryl ethers containing propyleneoxy or butyleneoxy groups instead of the ethyleneoxy groups in these compounds; diethylene glycol diphenyl ether, triethylene glycol diphenyl ether, tetraethylene glycol diphenyl ether, polyethylene glycol diaryl ethers wherein the phenyl groups in these compounds are substituted by an alkyl group, an alkoxy group, a halogen atom, etc., and polyalkylene glycol diaryl ethers such as polypropylene glycol diaryl ethers or polybutylene glycol diaryl ethers containing propyleneoxy or butyleneoxy groups instead of the ethyleneoxy groups in these compounds.

When a large amount of alkaline metal ions is present in the organic solvent, the depolymerization reaction system turns black within a short time and the glycolide to be distilled out is susceptible to contamination. If the content of alkaline metal ions in the depolymerization reaction system is 0.001% by mass or lower, and preferably less than 0.001% by mass, the depolymerization may then be carried out in a stable manner. To this end, however, it is desired to reduce the content of alkaline metal ions in the organic solvent itself as much as possible.

9. Solubilizer

With a view to enhancing the solubility characteristics (solubility and dissolution rate) of the glycolic acid oligomer in the organic solvent, a solubilizer may be used. The solubilizer used herein should preferably satisfy the following requirements:

(i) The solubilizer must have a boiling point higher than that of the organic solvent used for co-distillation of glycolide, i.e., a boiling point exceeding 450° C. so that upon depolymerization, it cannot possibly, or can hardly, be distilled out of the depolymerization reaction system. The use of a solubilizer having a boiling point of 450° C. or lower is not preferred because it is distilled out together with the organic solvent upon depolymerization, resulting in a decrease in the solubility characteristics of the glycolic acid oligomer in the depolymerization reaction system.

(ii) The solubilizer must have higher affinity for the glycolic acid oligomer than for the organic solvent. The affinity of the solubilizer for a glycolic acid oligomer may be indentifed by heating a mixture of the oligomer and an organic solvent to 230° C. to 280° C. to bring the concentration of the oligomer up to such a level that the mixture does not form any uniform solution phase, and then adding the solubilizer to the mixture system to make visual observation of whether the uniform solution phase is again formed or not.

For the solubilizer it is preferable to use non-basic organic compounds having functional groups such as OH, COOH, and CONH groups. Of these, compounds having hydroxyl groups (OH groups) are particularly preferred in view of dissolving power and stability. Non-basic organic compounds particularly suited for the solubilizer are monohydric or di- or poly-hydric alcohols (inclusive of their partially esterified or etherified products) and phenols. In particular, the alcohols provide the most effective solubilizers.

Among the alcohols, preference is given to polyalkylene glycols and polyalkylene glycol monoethers having the following formulae (2) and (3), respectively, as well as glycerin, tridecanol and decanediol.

(2)

Here $R^2$ is a methylene group or a straight-chain or branched-chain alkylene group having 2 to 8 carbon atoms and q is an integer of 1 or greater provided that when q is an integer of 2 or greater, a plurality of $R^2$s may be identical with or different from each other.

(3)

Here $R^3$ is a methylene group or a straight-chain or branched-chain alkylene group having 2 to 8 carbon atoms, X is a hydrocaron group and r is an integer of 1 or greater provided that when r is an integer of 2 or greater, a plurality of $R^3$s may be identical with or different from each other.

The polyalkylene glycol usable herein, for instance, includes polyethylene glycol, polypropylene glycol and polybutylene glycol. The polyalkylene glycol monoether usable herein, for instance, includes polyethylene glycol monoalkyl ethers such as polyethylene glycol monopropyl ether, polyethylene glycol monobutyl ether, polyethylene glycol monohexyl ether, polyethylene glycol monooctyl ether, polyethylene glycol monodecyl ether and polyethylene glycol monolauryl ether, and polyalkylene glycol monoalkyl ethers such as polypropylene glycol monoalkyl ethers or polybutylene glycol monoalkyl ethers wherein the ethyleneoxy groups in the aforesaid compounds are substituted by propyleneoxy or butyleneoxy groups. When, in the invention, the polyalkylene glycol monoether is used as the solubilizer, the cleaning effect on the wall surface of a reaction vessel or tank is much more enhanced.

The solubilizer should be used in an amount of usually 0.1 to 500 parts by mass, and preferably 1 to 300 parts by mass per 100 parts by mass of the glycolic acid oligomer. Too little a solubilizer is less than satisfactory in terms of solubilizing effect whereas too much is not economical because the recovery of the solubilizer costs much.

When a large amount of alkaline metal ions is present in the solubilizer, the depolymerization reaction system turns black and the glycolide to be distilled out is susceptible to contamination. For the purpose of reducing the content of alkaline metal ions in the depolymerization reaction system down to 0.001% by mass or lower, it is desired to reduce the content of alkaline metal ions in the solubilizer as much as possible.

10. High-Boling Non-Basic Organic Compound

It has now been found out that the high-boiling non-basic organic compound suitable for the aforesaid solubilizer and having a boiling point exceeding 450° C., even when used alone or not in combination with any organic solvent, has an action on the smooth progress of the depolymerization reaction of the glycolic acid oligomer.

For instance, the depolymerization reaction can be carried out in a stable manner by heating the glycolic acid oligomer and a non-basic organic compound having a boiling point exceeding 450° C. When the glycolic acid oligomer contains alkaline metal ions in an amount exceeding 0.001% by mass, the depolymerization reaction can be performed in a stable manner by heating the glycolic acid oligomer and non-basic organic compound in the presence of the sulfate and/or organic acid salt containing di- or poly-valent cations.

Heating should be carried out at a temperature of at least 230° C. at which the depolymerization reaction of the glycolic acid oligomer takes place. Heating may be done at a temperature higher than the boiling point of the non-basic organic compound; however, it is noted that even at a temperature lower than that boiling point, the depolymerization reaction proceeds smoothly due to the interaction with the glycolic acid oligomer. Heating should thus be carried out at a temperature in the range of preferably 230 to 320° C., more preferably 235 to 300° C., and even more preferably 240 to 290° C.

For the non-basic organic compound it is preferable to use the aforesaid polyalkylene glycols, polyalkylene glycol monoethers, glycerin, tridecanol, decanediol, etc., among which polyalkylene glycols such as polyethylene glycol, polypropylene glycol and polybutylene glycol are more preferred, although polyethylene glycol is most preferred.

These preferable non-basic organic compounds are liquid at normal temperature or at least 230° C. at which the depolymerization reaction of the glycolic acid oligomer takes place and at a temperature less than the boiling point, and so may be regarded as being a sort of polar organic solvent having a boiling point exceeding 450° C.

The non-basic organic compound is used in an amount of usually 0.1 to 500 parts by mass, and preferably 1 to 300 parts by mass per 100 parts by mass of the glycolic acid oligomer. When a depolymerization reaction system containing the glycolic acid oligomer and non-basic organic compound contains alkaline metal ions in an amount of at least 0.001% by mass for the reason that the glycolic acid oligomer contains alkaline metal ions or other reasons, a sulfate and/or an organic acid salts, each in the form of di- or poly-valent cation, should preferably be allowed to exist in such an amount as to be 1 to 100 times (on a mass basis) as large as the amount of alkaline metal ions present in the depolymerization reaction system.

For the sulfate in the form of di- or poly-valent cations, use may be made of at least one metal sulfate selected from the group consisting of magnesium sulfate, nickel sulfate, iron sulfates, copper sulfates, zinc sulfate, zirconium sulfate and aluminum sulfate, among which the iron sulfates are preferred, and ferric sulfate is particularly preferred. For the organic acid salt, use may be made of di- or poly-valent cationic salts of aliphatic acids, aromatic acids, etc. The organic acid that is a conjugate acid, for instance, includes aliphatic carboxylic acids such as formic acid, acetic acid, oxalic acid, malonic acid, succinic acid, glutaric acid, lactic acid, glycolic acid, butanoic acid, pentanoic acid, hexanoic acid, heptanoic acid, octanoic acid, dodecanoic acid, stearic acid and oleic acid; aromatic carboxylic acids such as phthallic acid, benzoic acid and salicylic acid; and so on. Of these, the aliphatic carboxylic acids are preferred, although particular preference is given to lactic acid and α-hydroxyacetic acid such as glycolic acid. For di- or poly-valent cations of the organic acid salts, for instance, reference is made to magnesium, nickel, iron, copper, zinc, zirconium, and aluminum. Usually but not exclusively, the cations are divalent, trivalent, or tetravalent. Of these organic acid salts, aluminum lactate is preferably used. These organic acid salts may be used alone or in combination of two or more or, alternatively, they may be used in combination with the sulfate.

11. Glycolic Acid Composition

For the synthesis of glycolic acid oligomers containing the sulfate and/or organic acid salt in the form of di- or poly-valent cations, it is preferable to use glycolic acid compositions containing the sulfate and/or organic acid salt in the form of di- or poly-valent cations. The glycolic acid composition used herein should contain the sulfate and/or organic acid salt in the form of di- or poly-valent cations in an amount of 0.01 to 10 grams, and preferably 0.02 to 5 grams per mole of glycolic acid. At less than the lower limit it is difficult to obtain the desired effect, and at greater than the upper limit the effect is no longer enhanced.

It is usually desired that glycolic acid be substantially free from any alkaline metal ion; however, this does not go true for the case where, for instance, the sulfate and/or organic acid salt in the form of di- or poly-valent cations are contained therein. Glycolic acid may be used in an aqueous solution form. In this case, however, the aqueous solution should contain glycolic acid in an amount of at least 10% by mass, preferably at least 15% by mass, and more preferably at least 20% by mass. At less than 10% by mass, a glycolic acid composition is susceptible to crystallization and so has difficulty in handling. Moreover, the dispersion of the sulfate and/or organic acid salt in the form of di- or poly-valent cations tends to become heterogeneous. At greater than 50% by mass, dehydration and drying steps become complicated and so energy consumption at each step does not only become excessive but also the polymer throughput per process tends to decrease.

EXAMPLES

The present invention is now explained more specifically with reference to synthesis examples, inventive examples and comparative examples.

Set out below are the measuring methods used herein.

1. Method of Quantification of Metal Ions

The quantification of metal ions was carried out by ICP emission spectral analysis. Precisely weighed 1 gram of a glycolic acid oligomer or a sample containing that oligomer was wet decomposed with sulfuric acid and a hydrogen peroxide solution. Deionized water was added to the decomposed product to prepare a solution having a volume regulated to 100 ml, which was then subjected to ICP analysis. The quantification limit to this method is 0.001% by mass.

2. Melting Point of Glycolic Acid Oligomer

The melting point of a glycolic acid oligomer was detected by heating its sample at a heating rate of 10° C. per minute in an inert gas atmosphere, using a differential scanning calorimeter (DSC).

Synthesis Example 1

1. Preparation of a Purified Aqueous Solution of Glycolic Acid

A commercially available industrial-grade aqueous solution of glycolic acid (a 70% by mass aqueous solution made by Du Pont) was purified through a column filled with a cation exchange resin.

2. Synthesis of Glycolic Acid Oligomer (A)

A 5-liter autoclave was charged with 2,500 grams of the (70% by mass) aqueous solution of glycolic acid purified as mentioned above. While stirred at normal pressure, the solution was heated from 170° C. to 200° C. over 2 hours for a condensation reaction during which the formed water was distilled out. Then, the internal pressure of the autoclave was lowered to 5.0 kPa, at which the solution was heated at 200° C. for 2 hours to distill off low-boiling materials such as unreacted glycolic acid, thereby obtaining 1,700 grams of glycolic acid oligomer (A), which was found to have a melting point of 206° C. and an alkaline metal ion content of less than 0.001% by mass.

Synthesis Example 2

Synthesis of Glycolic Acid Oligomer (B)

As in synthesis example 1, 1,650 grams of glycolic acid oligomer (B) were obtained with the exception that 3,570 grams of a commercially available industrial-grade aqueous solution of glycolic acid (a 70% by mass aqueous solution made by Du Pont) were used. This glycolic acid oligomer (B) was found to have a melting point of 202° C. and an alkaline metal ion content of 0.035% by mass.

Synthesis Example 3

1. Preparation of a Purified Aqueous Solution of Glycolic Acid

Glycolic acid oligomer (B) was synthesized following synthesis example 2. Charged with 5,800 grams of glycolic acid oligomer (B), 3 grams of p-toluenesulfonic acid and 16,000 grams of methanol, an autoclave was heated at 150° C. for 24 hours. After removal of excessive methanol, distillation was then carried out to obtain 8,100 grams of methyl glycolate that was found to have a melting point of 151° C. Two thousand seven hundred (2,700) grams of the thus obtained methyl glycolate were hydrolyzed in the presence of water in a ten-fold molar amount of 5,400 grams, thereby obtaining an aqueous solution of glycolic acid.

2. Synthesis of Glycolic Acid Oligomer

As in synthesis example 1, 1,550 grams of glycolic acid oligomer (C) were obtained with the exception that the purified aqueous solution of glycolic acid prepared as mentioned above was used. This glycolic acid oligomer (C) was found to have a melting point of 207° C. and an alkaline metal ion content of less than 0.001% by mass.

Synthesis Example 4

Synthesis of Polyalkylene Glycol Ether (TEGDME)

Commercially available polyethylene glycol dimethyl ether #250 (made by Merck) was distilled to synthesize tetraethylene glycol dimethyl ether having a polymerization degree of 4 (hereinafter abbreviated as TEGDME). The content of alkaline metal ions in this TEGDME was lower than the quantification limit (or less than 0.001% by mass, which means that the alkaline metal ions were not substantially contained therein, or they were not found or less the identification limit). The DEGDME was used as the solvent for the depolymerization reaction of the glycolic acid oligomer.

Example 1

Ten (10) grams of glycolic acid oligomer (A) prepared in synthesis example 1 were added to a 100-ml flask, which was then brought down to a pressure of 3 to 5 mmHg while heated to 260° C. for a depolymerization reaction. Distillates were cooled on ice water for trapping. After a 10-hour reaction, 7.2 grams of distillates were obtained whereas 2.8 grams of liquid components remained in the flask.

The 2.8-gram residual components were removed out of the flask and then rapidly cooled. Of the components, 1 gram was dissolved in hexafluoroisopropanol that was the solvent for the polyglycolic acid oligomer. Consequently, 0.53 gram was dissolved but 0.47 gram was not. As a result of analysis of 1 gram out of the residual components, it was found to have an alkaline metal ion content of less than 0.001% by mass. On the other hand, the 7.2-gram distillates were recrystallized from ethyl acetate, thereby recovering 5.8 grams of purified glycolide.

Example 2

1. Depolymerization Reaction

Sixty (60) grams of glycolic acid oligomer (A) prepared in synthesis example 1 and 400 grams of TEGDME were added to a 500-ml flask, which was then heated to 260° C. to thereby prepare a uniform solution with no phase separation. While kept at a temperature of 260° C., this solution was subjected-under reduced pressure to a depolymerization reaction, and TEGDME and a glycolide product were co-distilled out.

After a 5-hour depolymerization reaction, 362 grams of distillates were obtained. The distillates were then found to contain 38 grams of glycolide.

2. Experiment Wherein Depolymerization Reaction Was Repeated

Thirty-eight (38) grams of fresh glycolic acid oligomer (A) and 324 grams of fresh TEGDME (362 grams in all) were additionally fed into the reaction solution remaining in the flask, and the depolymerization reaction was then carried out at a temperature of 260° C. under reduced pressure. In this way, the depolymerization reaction was repeated while fresh TEGDME and glycolic acid oligomer in an amount corresponding to the amount of the distillates were added to the reaction solution remaining after the preceding depolymerization reaction.

After the depolymerization reaction was repeated ten times in this way, no substantial formation of heavy materials was found in the flask. After ten cycles of the depolymerization reaction were carried out, the reaction solution remaining in the flask was found by measurement to have an alkaline metal ion content of less than 0.001% by mass.

Example 3

1. Depolymerization Reaction

Sixty (60) grams of glycolic acid oligomer (A) prepared in synthesis example 1, 350 grams of TEGDME and 60 grams of deionized polyethylene glycol #400 (having an alkaline metal ion content of less than 0.001% by mass) acting as a solubilizer were added to a 500-ml flask, which was then heated to 260° C. to thereby prepare a uniform solution with no phase separation. While kept at a temperature of 260° C., this solution was subjected under reduced pressure to a depolymerization reaction, and TEGDME and a glycolide product were co-distilled out.

After a 5-hour depolymerization reaction, 362 grams of distillates were obtained. The distillates were then identified to contain 38 grams of glycolide.

2. Experiment Wherein Depolymerization Reaction Was Repeated

Thirty-eight (38) grams of fresh glycolic acid oligomer (A) and 324 grams of fresh TEGDME were additionally fed into the reaction solution remaining in the flask, and the depolymerization reaction was then carried out at a temperature of 260° C. under reduced pressure. In this way, the depolymerization reaction was repeated while fresh TEGDME and glycolic acid oligomer in an amount corresponding to the amount of the distillates were added to the reaction solution remaining after the preceding depolymerization reaction.

After the depolymerization reaction was repeated ten times in this way, no substantial formation of heavy materials was found in the flask. After ten cycles of the depolymerization reaction were performed, the reaction solution remaining in the flask was found by measurement to have an alkaline metal ion content of less than 0.001% by mass.

Example 4

As in example 3, the depolymerization reaction was repeated with the exception that glycolic acid oligomer (C) prepared in synthesis example 3 was used instead of glycolic acid oligomer (A).

After the depolymerization reaction was repeated 20 times in this way, no substantial formation of heavy materials was found in the flask. Hardly was there any increase in the volume of the remaining reaction. After 20 cycles of the depolymerization reaction were conducted, the reaction solution remaining in the flask was found by measurement to have an alkaline metal ion content of less than 0.001% by mass.

Comparative Example 1

Ten (10) grams of glycolic acid oligomer (B) obtained in synthesis example 2 were added to a 100-ml flask, which was then brought down to a pressure of 3 to 5 mmHg while heated to 260° C. for a depolymerization reaction. Distillates were cooled on ice water for trapping. Two hours after the start of the reaction, it was observed that black materials got mingled in the distillates.

After a 10-hour reaction, 3.7 grams of distillates were obtained whereas 6.3 grams of liquid components remained in the flask. The 6.3-gram residual components were removed out of the flask and then rapidly cooled. Of the components, 1 gram was dissolved in hexafluoro-isopropanol that was the solvent for the glycolic acid oligomer. Consequently, 0.51 gram was dissolved but 0.49 gram was not. As a result of analysis of 1 gram out of the residual components, it was found to have an alkaline metal ion content of 0.055% by mass. Two point eight (2.8) grams of slightly colored glycolide were recovered from 3.7 grams of colored distillates by recrystallizing them from ethyl acetate. The amount of the recovered glycolide was only roughly 50% of 5.8 grams in example 1.

Comparative Example 2

Sixty (60) grams of glycolic acid oligomer (B) obtained in synthesis example 2 and 400 grams of TEGDME were added to a 500-ml flask, which was then heated to 260° C. to thereby prepare a uniform solution with no phase separation. While kept at a temperature of 260° C., this solution was subjected under reduced pressure to a depolymerization reaction, and TEGDME and a glycolide product were co-distilled out.

After a 3-hour depolymerization reaction, some considerable blackening of the reaction solution in the flask was observed with deposition of heavy materials on the inner wall of the flask and coloration of distillates, and so the depolymerization reaction was terminated. After the reaction, the reaction solution remaining in the flask was found by measurement to have an alkaline metal ion content of 0.005% by mass.

Comparative Example 3

To learn the influence of alkaline metal ions on the depolymerization reaction, 60 grams of glycolic acid oligomer (A) prepared in synthesis example 1, 400 grams of TEGDME and 0.1 gram of sodium chloride (NaCl) were added to a 500-ml flask, which was in turn heated to 260° C. to thereby prepare a uniform solution with no phase separation. While kept at a temperature of 260° C., this solution was subjected under reduced pressure to a depolymerization reaction, and TEGDME and a glycolide product were co-distilled out.

After a 2-hour depolymerization reaction, some considerable blackening of the reaction solution in the flask was observed with deposition of heavy materials on the inner wall of the flask and coloration of distillates, and so the depolymerization reaction was terminated. After the reaction, the reaction solution remaining in the flask was found by measurement to have an alkaline metal ion content of 0.010% by mass.

Example 5
Preparation of Glycolic Acid Compositions GA1 to GA7

Zero point five (0.5) gram of each of the sulfates, shown in Table 1, in the form of di- or poly-valent cations was added to 108.6 grams (1 mole of glycolic acid) of the purified aqueous solution of glycolic acid (a 70% by mass aqueous solution) prepared in example 1. In this way, seven glycolic acid compositions GA1 to GA7 were prepared. The type of the sulfate added, the content of alkaline metal ions and the amount of di- or poly-valent cations present per 1 mole of glycolic acid are shown in Table 1.

TABLE 1

| Composition | GA1 | GA2 | GA3 |
|---|---|---|---|
| Content of AMI* (%) | <0.001 | <0.001 | <0.001 |
| Sulfate | $MgSO_4 \cdot 7H_2O$ | $Fe_2(SO_4)_3 \cdot 9H_2O$ | $CuSO_4 \cdot 5H_2O$ |
| Amount of Cations** (g) | 0.049 | 0.099 | 0.127 |
| Composition | GA4 | GA5 | GA6 |
| Content of AMI* (%) | <0.001 | <0.001 | <0.001 |
| Sulfate | $NiSO_4 \cdot 6H_2O$ | $ZnSO_4 \cdot 7H_2O$ | $ZrSO_4 \cdot 4H_2O$ |
| Amount of Cations** (g) | 0.116 | 0.114 | 0.128 |

| Composition | GA7 |
|---|---|
| Content of AMI* (%) | <0.001 |
| Sulfate | $AlSO_4$ |
| Amount of Cations** (g) | 0.158 |

AMI*: alkaline metal ions
Cations**: the amount of di- or poly-valent cations per mole of glycolic acid Synthesis Examples 4–10
Synthesis of Glycolic Acid Oligomers (D) to (J)

Glycolic acid oligomers (D) to (J) were synthesized as in synthesis example 1 with the exception that glycolic acid compositions GA1 to GA7 prepared in example 5 were used instead of the purified glycolic acid. Similar synthesis was repeated until the required amount of oligomer was reached, thereby synthesizing the necessary amount of oligomer. The melting points of the thus obtained glycolic acid oligomers (D) to (J), the contents of alkaline metal ions therein and the contents of di- or poly-valent cations therein are set out in Table 2.

Example 6
Preparation of Glycolic Acid Compositions GA8 to GA14

Seven glycolic acid compositions GA8 to GA14 were prepared by charging a 5-liter autoclave with 3,570 grams of a commercially available industrial-grade aqueous solution of glycolic acid (a 70% by mass aqueous solution made by Du Pont) and adding thereto the same sulfates as listed in Table 1 in the form of di- or poly-valent cations, each used in an amount of 40 grams.

Synthesis Examples 11–17
Synthesis of Glycolic Acid Oligomers (K) to (O)

Each of glycolic acid compositions GA8 to GA14 prepared in example 6 was heated from 170° C. to 200° C. over 2 hours while it was stirred under normal pressure for a condensation reaction during which the formed water was distilled out. Then, the internal pressure of the autoclave was brought down to 5.0 kPa and the reaction product was heated at 200° C. for 2 hours while low-boiling materials such as unreacted glycolic acid were distilled off. In this way, glycolic acid oligomers (K) to (Q) were synthesized.

The type of the sulfates used in the form of di- or poly-valent cations, the melting point of each oligomer, the content of alkaline metal ions and the mass ratio of the content of di- or poly-valent cations to the content of alkaline metal ions are set out in Table 2. It is noted that the melting point of glycolic acid oligomer (B) obtained in synthesis example 2 and the content of alkaline metal ions therein, too, are reported in Table 2.

TABLE 2

| Synthesis Example | Glycolic Acid Composition | Oligomer | Melting Point (° C.) | Content of AMI* (%) |
|---|---|---|---|---|
| 2 | — | B | 202 | 0.035 |
| 4 | GA1 | D | 209 | <0.001 |
| 5 | GA2 | E | 209 | <0.001 |
| 6 | GA3 | F | 208 | <0.001 |
| 7 | GA4 | G | 207 | <0.001 |
| 8 | GA5 | H | 209 | <0.001 |
| 9 | GA6 | I | 206 | <0.001 |
| 10 | GA7 | J | 208 | <0.001 |
| 11 | GA8 | K | 203 | 0.035 |
| 12 | GA9 | L | 202 | 0.035 |
| 13 | GA10 | M | 204 | 0.035 |
| 14 | GA11 | N | 203 | 0.035 |
| 15 | GA12 | O | 203 | 0.035 |
| 16 | GA13 | P | 202 | 0.035 |
| 17 | GA14 | Q | 203 | 0.035 |

| Synthesis Example | Di- or Poly-Valent Cation | | Mass Ratio of Di- or Poly-Valent Cations/AMI* |
|---|---|---|---|
| | Type | Content (%) | |
| 2 | — | 0 | 0 |
| 4 | $Mg^{2+}$ | 0.094 | — |
| 5 | $Fe^{3+}$ | 0.192 | — |
| 6 | $Cu^{2+}$ | 0.245 | — |
| 7 | $Ni^{2+}$ | 0.224 | — |
| 8 | $Zn^{2+}$ | 0.221 | — |
| 9 | $Zr^{4+}$ | 0.248 | — |
| 10 | $Al^{3+}$ | 0.305 | — |
| 11 | $Mg^{2+}$ | 0.114 | 3.3 |
| 12 | $Fe^{3+}$ | 0.233 | 6.7 |
| 13 | $Cu^{2+}$ | 0.298 | 8.5 |
| 14 | $Ni^{2+}$ | 0.272 | 7.8 |
| 15 | $Zn^{2+}$ | 0.268 | 7.7 |
| 16 | $Zr^{4+}$ | 0.301 | 8.6 |
| 17 | $Al^{3+}$ | 0.371 | 10.6 |

AMI*: alkaline metal ions

Example 7

Ten (10) grams of glycolic acid oligomer (D) synthesized in synthesis example 4 were added to a 100-ml flask, which was then brought down to a pressure of 3 to 5 mmHg while heated to 260° C. for a depolymerization reaction. Distillates were cooled on ice water for trapping. After a 10-hour reaction, 7.3 grams of distillates were obtained whereas 2.7 grams of liquid components remained in the flask.

The 2.7-gram residual components were removed out of the flask and then rapidly cooled. Of the components, 1 gram was dissolved in hexafluoroisopropanol that was the solvent for the polyglycolic acid oligomer. Consequently, 0.52 gram was dissolved but 0.48 gram was not. As a result of analysis of 1 gram out of the residual components, it was found to have an alkaline metal ion content of less than 0.001% by mass. On the other hand, the 7.3-gram distillates were recrystallized from ethyl acetate, thereby recovering 5.8 grams of purified glycolide.

Example 8

1. Depolymerization Reaction

Sixty (60) grams of glycolic acid oligomer (E) prepared in synthesis example 5, 350 grams of TEGDME and 60 grams of deionized polyethylene glycol #400 (having an alkaline metal ion content of less than 0.001% by mass) acting as a solubilizer were added to a 500-ml flask, which was then heated to 260° C. to thereby prepare a uniform solution with no phase separation. While kept at a temperature of 260° C., this solution was subjected under reduced pressure to a depolymerization reaction, and TEGDME and a glycolide product were co-distilled out.

After a 5-hour depolymerization reaction, 362 grams of distillates were obtained. The distillates were then found to contain 38 grams of glycolide.

2. Experiment Wherein Depolymerization Reaction Was Repeated

Thirty-eight (38) grams of fresh glycolic acid oligomer (E) and 324 grams of fresh TEGDME were additionally fed into the reaction solution remaining in the flask, and the depolymerization reaction was then carried out at a temperature of 260° C. under reduced pressure. In this way, the depolymerization reaction was repeated while fresh TEGDME and glycolic acid oligomer in an amount corresponding to the amount of the distillates were added to the reaction solution remaining after the preceding depolymerization reaction.

After the depolymerization reaction was repeated twenty times in this way, no substantial formation of heavier matters was found in the flask. Hardly was any increase in the volume of the remaining reaction solution found.

3. Recovery of Glycolide

After the depolymerization reaction was repeated 28 times in this way, the distillates, to which a two-fold volume of cyclohexane was added, was let stand alone overnight to allow glycolide crystals to separate out. The crystals were filtered out, and washed with cyclohexane. The crystals were further recrystallized from ethyl acetate and dried under reduced pressure, so that purified glycolide was recovered. The results are reported in Table 3.

Examples 9–20

Depolymerization reactions were repeated as in example 8 with the exception that glycolic acid oligomers (F) to (Q) synthesized in synthesis examples 6 to 17 were used instead of glycolic acid oligomer (E), and purified glycolides were then recovered. The results of experimentation inclusive of the number of repetition of depolymerization reaction are reported in Table 3. It is noted that the yields, g and %, of glycolide recovered in comparative example 2 as mentioned above, too, are reported in Table 3.

TABLE 3

| | Oligomer | NORD* | Charged Oligomer (g) | Glycolide, (g) | Yields (%) |
|---|---|---|---|---|---|
| Ex. 8 | E | 28 | 1,120 | 930 | 83.0 |
| Ex. 9 | F | 27 | 1,080 | 918 | 85.0 |
| Ex. 10 | G | 29 | 1,150 | 960 | 83.5 |
| Ex. 11 | H | 28 | 1,090 | 922 | 84.6 |
| Ex. 12 | I | 27 | 1,075 | 925 | 86.0 |
| Ex. 13 | J | 28 | 1,105 | 930 | 84.2 |
| Ex. 14 | K | 21 | 850 | 710 | 83.5 |
| Ex. 15 | L | 22 | 880 | 724 | 82.3 |
| Ex. 16 | M | 20 | 810 | 700 | 86.4 |
| Ex. 17 | N | 21 | 840 | 710 | 84.5 |
| Ex. 18 | O | 20 | 800 | 698 | 87.3 |
| Ex. 19 | P | 21 | 830 | 708 | 85.3 |
| Ex. 20 | Q | 22 | 880 | 731 | 83.1 |
| Comp. Ex. 2 | B | 1 | 60 | 28 | 46.7 |

NORD*: the number of repetition of depolymerization

Example 21

1. Depolymerization Reaction

To learn the influence of alkaline metal ions on the depolymerization reaction, 60 grams of glycolic acid oligomer (E) synthesized in synthesis example 5, 0.01 gram of sodium chloride (NaCl), 400 grams of TEGDME and deionized polyethylene glycol #400 were added to a 500-ml flask, which was in turn heated to 260° C. to thereby prepare a uniform solution with no phase separation. While kept at a temperature of 260° C., this solution was subjected under reduced pressure to a depolymerization reaction, and TEGDME and a glycolide product were co-distilled out.

After the depolymerization reaction was carried out for 5 hours in this way, 369 grams of distillates were obtained. These distillates were identified to contain 42 grams of glycolide.

2. Experiment Wherein Depolymerization Reaction Was Repeated

Forty (40) grams of fresh glycolic acid oligomer (E) and 320 grams of fresh TEGDME were additionally fed into the reaction solution remaining in the flask, and the depolymerization reaction was then carried out at a temperature of 260° C. under reduced pressure. In this way, the depolymerization reaction was repeated while fresh TEGDME and glycolic acid oligomer in an amount corresponding to the amount of the distillates were added to the reaction solution remaining after the preceding depolymerization reaction.

After the depolymerization reaction was repeated twenty times in this way, no substantial formation of heavier matters was found in the flask. Hardly was any increase in the volume of the remaining reaction solution found.

Comparative Example 4

Ten (10) grams of glycolic acid oligomer (B) synthesized in synthesis example 2 and 2.5 grams of polyethylene glycol #100 (having an average molecular weight of 1,000) deionized with an ion exchange resin were added to a 100-ml flask, which was then brought down to a pressure of 3 to 5 mmHg while heated to 260° C. for a depolymerization reaction. Distillates were cooled on ice water for trapping. After a 3-hour reaction, it was observed that black materials got mingled in the distillates.

After a 10-hour reaction, 5.5 grams of distillates were obtained whereas 7.0 grams of liquid components remained in the flask. As a result of quantification of 1 gram out of the residual components, it was found to have an alkaline metal ion content of 0.05% by mass. On the other hand, 4.0 grams of purified glycolide were recovered by recrystallization of the liquid distillates from ethyl acetate. This amount of glycolide was roughly 70% of 5.8 grams in example 1.

Example 22

Ten (10) grams of glycolic acid oligomer (B) synthesized in synthesis example 2, 2.5 grams of polyethylene glycol #100 (having an average molecular weight of 1,000) deionized with an ion exchange resin and 0.05 grams of ferric sulfate. $9H_2O$ were added to a 100-ml flask, which was then brought down to a pressure of 3 to 5 mmHg while heated to 260° C. for a depolymerization reaction. Distillates were cooled on ice water for trapping.

After a 10-hour reaction, 7.5 grams of distillates with no black materials formed were obtained whereas 5.0 grams of liquid components remained in the flask. As a result of quantification of 1 gram out of the residual components, it was found to have an alkaline metal ion content of 0.07% by mass. On the other-hand, 5.7 grams of purified glycolide were recovered by recrystallization of the liquid distillates from ethyl acetate. This amount of glycolide was nearly the same as 5.8 grams in example 1.

Example 23

Preparation of Glycolic Acid Composition GA15

A 5-liter autoclave was charged with 3,570 grams of a commercially available industrial-grade aqueous solution of glycolic acid (a 70% by mass aqueous solution made by Du Pont) together with 40 grams of aluminum lactate (made by Kanto Chemicals), thereby preparing glycolic acid composition GA15.

Synthesis Example 18

Synthesis of Glycolic Acid Oligomer (R)

Glycolic acid composition GA15 prepared in example 23 was heated from 170° C. to 200° C. over 2 hours while it was stirred under normal pressure for a condensation reaction during which the formed water was distilled out. Then, the internal pressure of the autoclave was brought down to 5.0 kPa and the reaction product was heated at 200° C. for 2 hours while low-boiling materials such as unreacted glycolic acid were distilled off. In this way, glycolic acid oligomer (R) was synthesized. The melting point of the oligomer, the content of alkaline metal ions and the mass ratio of the content of aluminum ions to the content of alkaline metal ions are set out in Table 4.

TABLE 4

| Synthesis Example | Glycolic Acid Comp. | Oligomer | Melting Point (° C.) | Content of Alkaline Metal Ions (%) |
|---|---|---|---|---|
| 18 | GA15 | R | 208 | 0.035 |

| Synthesis Example | Di- or Poly-Valent Cations | | Mass Ratio of Di- or Poly-Valent Cations/AMI* |
|---|---|---|---|
| | Type | Content (%) | |
| 18 | $Al^{3+}$ | 0.203 | 5.79 |

AMI*: alkaline metal ions

Example 24

The depolymerization reaction was repeated as in example 8 with the exception that glycolic acid oligmer (R) synthesized in synthesis example 18 was used instead of glycolic acid oligomer (E), and purified glycolide was recovered. The results of experimentation inclusive of the number of repetition of depolymerization reaction are reported in Table 5.

TABLE 5

| | | | Amount of Charged | Yields | |
|---|---|---|---|---|---|
| | Oligomer | NRD* | Oligomer (g) | (g) | (%) |
| Ex. 23 | R | 20 | 810 | 702 | 86.7 |

NRD*: the number of repetition of depolymerization

Advantages of the Invention

The present invention provides a process for the production of glycolide by depolymerization of glycolic acid oligomers, which enables depolymerization reactions to be carried out in a stable manner so that glycolide can be produced economically yet efficiently. The production process of the invention is well suited for mass production of glycolide by carrying out depolymerization reactions continuously or repeatedly.

The present invention also provides a glycolic acid composition that is the raw material for glycolic acid oligomers, which ensures stable depolymerization reactions.

The glycolide obtained by the production process of the invention, for instance, is well suited for the starting material for polyglycolic acid (i.e., polyglycolide) and glycolic acid copolymers which are useful biodegradable polymers, medical polymers, etc.

We claim:

1. A process for producing glycolide by depolymerization by heating of a glycolic acid oligomer in the presence or absence of a solvent, wherein:

a depolymerization reaction is carried out while:

(1) the content of alkali metal ions in a glycolic acid oligomer-containing depolymerization reaction system is controlled to 0.001% by mass or lower, (2) a sulfate or an organic acid salt, each in the form of divalent or other polyvalent cations, or a mixture thereof is allowed to be present as a stabilizer in the depolymerization reaction system, or (3) the content of alkali metal ions in the depolymerization reaction system is controlled to 0.001% by mass or lower, and a sulfate or an organic acid salt, each in the form of divalent or other polyvalent cations, or a mixture thereof is allowed to be present as a stabilizer in the depolymerization reaction system.

2. The production process according to claim 1, wherein the amount of alkali metal ions contained in the glycolic acid oligomer is controlled to 0.001% by mass or lower, whereby the content of alkali metal ions in the depolymerization reaction system is controlled to 0.001% by mass or lower.

3. The production process according to claim 1, wherein a sulfate or an organic acid salt, each in the form of divalent or other polyvalent cations, or a mixture thereof is contained in the glycolic acid oligomer, thereby allowing the sulfate or the organic acid salt, each in the form of divalent or other polyvalent cations, or the mixture thereof to be present in the depolymerization reaction system.

4. The production process according to claim 3, wherein the glycolic acid oligomer is formed by a condensation reaction of a glycolic acid composition comprising glycolic acid and a sulfate or an organic acid salt, each in the form of divalent or other polyvalent cations, or a mixture thereof, thereby allowing the sulfate or the organic acid salt, each in the form of divalent or other polyvalent cations, or the mixture thereof to be contained in the glycolic acid oligomer.

5. The production process according to claim 1, wherein the organic acid salt in the form of divalent or other polyvalent cations is an aliphatic carboxylic acid salt.

6. The production process according to claim 1, wherein the organic acid salt in the form of divalent or other polyvalent cations is an α-hydroxyacetic acid salt.

7. The production process according to claim 1, wherein the organic acid salt in the form of divalent or other polyvalent cations is at least one organic acid salt selected from the group consisting of aluminum lactate and aluminum glycolate.

8. The production process according to claim 1, wherein the sulfate in the form of divalent or other polyvalent cations is at least one metal sulfate selected from the group consisting of magnesium sulfate, nickel sulfate, iron sulfates, copper sulfates, zinc sulfate, zirconium sulfate, and aluminum sulfate.

9. The production process according to claim 1, wherein the depolymerization reaction system contains as a stabilizer 0.001 to 5% by mass of a sulfate or an organic acid salt, each in the form of divalent or other polyvalent cations, or a mixture thereof.

10. The production process according to claim 1, wherein the depolymerization reaction system is composed substantially of a glycolic acid oligomer alone, and free from any solvent.

11. The production process according to claim 1, wherein the depolymerization reaction system comprises a glycolic acid oligomer and a solvent.

12. The production process according to claim 11, wherein the solvent has an alkali metal ion content of 0.001% by mass or lower.

13. The production process according to claim 1, wherein the process for producing glycolide by depolymerization by heating of a glycolic acid oligomer in the presence or absence of a solvent comprises a succession of steps of:

(I) heating under normal pressure or reduced pressure a mixture comprising a glycolic acid oligomer and an organic solvent having a boiling point of 230 to 450° C., thereby dissolving the glycolic acid oligomer in the organic solvent until the proportion of a glycolic acid oligomer melt phase in the mixture is reduced down to 0.5 or lower, (II) heating under normal pressure or reduced pressure a solution obtained at step (I) for depolymerization of the glycolic acid oligomer, and glycolide formed by the depolymerization is distilled together with the organic solvent out of the depolymerization reaction system, and (III) the glycolide is recovered from distillates obtained by the distillation.

14. The production process according to claim 13, wherein at step (I), a non-basic organic compound having a boiling point exceeding 450° C. is added as a solubilizer to the mixture to thereby dissolve the glycolic acid oligomer in the organic solvent.

15. The production process according to claim 14, wherein the solubilizer has an alkali metal ion content of 0.001% by mass or lower.

16. The production process according to claim 13, wherein at step (II), a fresh glycolic acid oligomer and a fresh organic solvent are additionally fed into the depolymerization reaction system during or after the glycolide and organic solvent are distilled out, thereby carrying out depolymerization continuously or repeatedly.

17. The production process according to claim 1, wherein the process for producing glycolide by depolymerization by heating of a glycolic acid oligomer in the presence or absence of a solvent comprises depolymerization by heating of a mixture of a glycolic acid oligomer and a non-basic organic solvent having a boiling point exceeding 450° C. in the presence of a sulfate or an organic acid salt, each in the form of divalent or other polyvalent cations, or a mixture thereof.

18. The production process according to claim 17, wherein the non-basic organic compound is a polar organic solvent having a boiling point exceeding 450° C.

19. The production process according to claim 18, wherein the polar organic solvent is a polyalkylene glycol.

20. The production process according to claim 1, wherein the sulfate or organic acid salt, each in the form of divalent or other polyvalent cations, or a mixture thereof is allowed to be present in such a way that the amount of divalent or other polyvalent cations is in the range of, on a mass basis, 1 to 100 times as large as the amount of alkali metal ions present in the depolymerization reaction system.

21. A glycolic acid composition comprising at least 10% by mass of water and comprising an organic acid salt in the form of divalent or other polyvalent cations.

22. The glycolic acid composition according to claim 21, which contains a sulfate or an organic acid salt, each in the form of divalent or other polyvalent cations, or a mixture thereof in an amount of 0.01 to 10 grams per mole of glycolic acid.

23. A glycolic acid composition, which contains a sulfate or an organic acid salt, each in the form of divalent or other polyvalent cations, or a mixture thereof in an amount of 0.01 to 10 grams per mole of glycolic acid.

24. The production process according to claim 13, wherein the sulfate or organic acid salt, each in the form of divalent or other polyvalent cations, or a mixture thereof is allowed to be present in such a way that the amount of divalent or other volyvalent cations is in the range of, on a mass basis, 1 to 100 times as large as the amount of alkali metal ions present in the depolymerization reaction system.

25. The production process according to claim 17, wherein the sulfate or organic acid salt, each in the form of divalent or other polyvalent cations, or a mixture thereof is allowed to be present in such a way that the amount of divalent or other polyvalent cations is in the range of, on a mass basis, 1 to 100 times as large as the amount of alkali metal ions present in the depolymerization reaction system.

* * * * *